US006062225A

United States Patent [19]
Keefe et al.

[11] Patent Number: 6,062,225
[45] Date of Patent: May 16, 2000

[54] DETERMINING ION FLUX OF EMBRYOS AND OOCYTES

[75] Inventors: David L. Keefe, Newport, R.I.; Peter J. S. Smith, Falmouth, Mass.

[73] Assignee: Marine Biological Laboratory, Woods Hole, Mass.

[21] Appl. No.: 08/732,618

[22] Filed: Oct. 16, 1996

[51] Int. Cl.[7] .................................................. H61B 19/00
[52] U.S. Cl. ........................................... 128/898; 600/300
[58] Field of Search .................................. 600/33, 34, 35, 600/300, 551; 128/898; 606/119; 601/46

[56] References Cited

PUBLICATIONS

Kline et al. "Ion Currents and Membrane Domains in the Cleaving Xenopus Egg" J of Cell Biol 97:1753–1761, Dec. 1983.

Nuccitelli et al. "Polarity of Isolated Blastomeres Form Mouse Morulae: Detection of Trnascellular Currents" Dev Biol 109(2):452–63, Jun. 1985.

Hush et al. "A Calcium Influx Precedes Organogenesis in Graptopetalum" Plant Cell And Environ 14(7), Sep. 1991.

Zivkovic et al. "Localized Activity of CA2+–Stimulated Atpase and Transcellular Ionic Currents During Mesoderm Induction in Embryos of Lymnaea Stagnalis (Mollusca)" Roux's Arch Dev Biol 200: 320–9, 1991.

Dumoulin, J.C.M. et al., *Human Reproduction*, vol. 8, No. 9, 1993, "Temporal Effects of Ouabain on In–Vitro Development of Mouse Zygotes", pp. 1469–1474.

Eckert, A., et al., *Life Sciences*, vol. 55, Nos. 25/26, 1994, Alteration of Intracellular Calcium Regulation During Aging and Alzheimer's Disease in Nonneuronal Cells, pp. 2019–2029.

Keefe, D.L., et al. *Fertility and Sterility*, vol. 64, No. 3, Sep. 1995, Mitochondrial Deoxyribonucleic Acid Deletions in Oocytes and Reproductive Aging in Women, pp. 577–583.

Keefe, D.L., et al., *Reports From the MBL General Scientific Meetings,* Oct./Nov. 1995, "Identification of Calcium Flux in Single Preimplantation Mouse Embryos with the Calcium–Sensitive Vibrating Probe", p. 200.

Kuhtreiber, W.M. and Jaffe, L.F., *Journal of Cell Biology*, vol. 110, May 1990, "Detection of Extracellular Calcium Gradients with a Calcium–Specific Vibrating Electrode", pp. 1565–1573.

Overstrom, E.W. et al., *Journals of Reproduction & Fertility Ltd*, 1989, Synthesis of $Na^+/K^+$ AtPase by the Preimplantation Rabbit Blastocyst, pp. 283–295.

Rasmussen, M.D., Ph.D., H., *The New England Journal of Medicine*, vol. 314, No. 17, Apr. 24, 1986, "The Calcium Messenger System", pp. 1094–1132.

Robinson, D.H., and Benos, D.J., *Current Topics on Membranes*, vol. 39, Chapter 4, "Ion and Solute Transport in Preimplantation Mammalian Embryos", pp. 121–149.

Smith, P.J.S., *Nature*, vol. 378 Dec. 7, 1995, "Non–Invasive Ion Probes—Tools for Measuring Transmembrane Ion Flux", pp. 645–646.

Smith, P.J.S., et al., *Methods in Cell Biology*, vol. 40, Chapter 5, The Vibrating $Ca^{2+}$ Electrode: A New Technique for Detecting Plasma Membrane Regions of $Ca^{2+}$ Influx and Efflux, pp. 115–134.

vom Saal, F.S. et al., *The Physiology of Reproduction*, Second Edition, Chapter 61, "Natural History and Mechanisms of Reproductive Aging in Humans, Laboratory Rodents, and Other Selected Vertebrates", pp. 1213–1314.

*Primary Examiner*—Mickey Yu
*Assistant Examiner*—Kelly O'Hara
*Attorney, Agent, or Firm*—Hale and Dorr LLP

[57] ABSTRACT

A non-invasive self-referencing ion-sensitive probe is used to measure ion efflux from an embryo or an oocyte to determine viability and developmental potential.

12 Claims, No Drawings

6,062,225

DETERMINING ION FLUX OF EMBRYOS AND OOCYTES

STATEMENT OF GOVERNMENT RIGHTS

This invention was made with government funding under grant nos. K08-HD01099 and P41-RR01395 from the National Institutes of Health. The government may have some rights in this invention.

BACKGROUND OF THE INVENTION

Although aging affects nearly every aspect of female reproduction, oocytes are believed to be particularly affected by the aging process. Because many women delay marriage and childbearing until they are in their late thirties, the effects of aging on fertility has become increasingly significant. For those women who have difficulty conceiving, there are a number of options available, including oocyte donation and in vitro fertilization. Because fertility problems can cause great anguish and expense, however, it would be desirable to better understand the possibility of success of these different options to help women make informed decisions.

SUMMARY OF THE INVENTION

The present invention includes a method for determining the developmental potential of an embryo or an oocyte by measuring the ion flux, preferably transmembrane steady-state calcium efflux, from the embryo or oocyte. The measurement is preferably made with a non-invasive ion-sensitive vibrating probe that uses a calcium ionophore. With this determination about developmental potential, a woman can decide whether to use a particular oocyte of her own or to implant a particular embryo. The present invention also includes methods for establishing for an oocyte or an embryo a threshold or baseline of flux against which subsequent oocytes or embryos can be compared.

This method has particular importance for women having difficulty conceiving. By making a determination about the developmental potential of an oocyte prior to fertilization and/or an embryo prior to implantation, the diagnosis of reproductive ability is greatly improved because women can use the information to decide whether to depend on their own oocytes and pursue reproductive therapies that may be costly, or to pursue alternatives such as adoption or oocyte donation. While the present invention is described particularly in connection with humans and reproductive options, this method can be used for other mammals.

DETAILED DESCRIPTION

According to the present invention, a non-invasive ion-selective vibrating probe is used to measure ion flux, preferably the steady-state transmembrane calcium flux, in an oocyte or an embryo. This type of vibrating probe is known and is described in several sources, including Smith, "Non-invasive Ion Probes—Tools for Measuring Transmembrane Flux," *Nature,* Dec. 7, 1995; and in more detail in Smith, et. al., "The Vibrating $Ca^{2+}$ Electrode: A New Technique for Detecting Plasma Membrane Regions of $Ca^{2+}$ Influx and Efflux," *Methods in Cell Biology,* Vol. 40, pp. 115–134 (1994), both of which are expressly incorporated by reference for all purposes. The latter article provides the probe's history, development, manufacture, circuitry, and method of operation.

Experiments performed on mouse embryos showing that measurements of calcium flux and the resulting calcium flux signal can be used as a diagnostic to determine if the embryos are morphologically capable of further cleavage are described in Keefe, et. al., "Identification of Calcium Flux in Single Preimplantation Mouse Embryos with the Calcium Sensitive Vibrating Probe", Biol. Bull. 189:200 (October/November, 1995), which is expressly incorporated by reference for all purposes.

As described in the article about the mouse experiments, after hybrid matings (B6C3F1×B6D2F1), mouse embryos were removed surgically at the two-cell stage and either studied at this stage or cultured to the four-cell or eight-cell stage in M2 medium supplemented with 0.4% BSA at 37° C. in 5% $CO_2$. The two-cell stage embryos were washed at least twice in a modified M2 medium containing only 50 micromolar calcium and then transferred in the same medium to petri dishes coated with high-molecular weight polylysine to which the embryos adhered. The embryos were then measured for steady-state transmembrane calcium flux at room temperature (i.e., about 22° C.).

Measurement of the voltages associated with steady-state transmembrane calcium flux were performed in a manner as generally described in the incorporated Smith, et. al. article. After calibration to determine Nernstian characteristics, the probe was positioned within about 1 micron of an embryo's zona pellucida. The distribution of the calcium flux was mapped by moving the probe to at least four quadrants of the embryo's circumference. Images of the embryos were recorded with a video printer so that morphology could be correlated with steady-state calcium flux.

After this experimentation, embryos were routinely returned to normal M2 medium and kept at 37° C. in 5% $CO_2$, where cell division was monitored, i.e., they were returned to conditions to promote cell division. After observing the results of the cell division, the embryos were categorized into two classes:

(1) those morphologically normal and capable of further cleavage; and (2) those morphologically fragmented and incapable of further cleavage.

In the case of the first class of embryos, a strong calcium efflux signal was measured in all cases. In ten (10) preparations this efflux signal had a mean amplitude of −21.22 microvolts±5.7 (mean±standard deviation; the negative sign indicates an efflux as opposed to an influx). A value of about −20 microvolts corresponds to about 1 picomoles per $cm^2$ per second. Initial observations from the four quadrants did not exhibit substantial differences in the level of microvolts recorded, i.e., there was no observable polarity.

In class 2 embryos there was no measurable calcium efflux signal. Of five (5) embryos examined, the signal at the plasma membrane had a mean amplitude of −1.75 microvolts±5.28. Considering a background noise of 2.07 microvolts±2.24, the measurements were within the noise range and thus substantially zero.

For a group of embryos, therefore, the calcium flux signal is diagnostic of ability of further cleavage, and one can establish a threshold or baseline against which the calcium flux of subsequent embryos is compared to determine such ability. In this case, for example, one could determine that the mean of 21.2 minus the deviation of 5.7, i.e., about −15.5 microvolts, is a good low threshold for class 1 embryos; that the mean of 1.75 plus the deviation of 5.28, i.e., about −7.0 microvolts, is an upper threshold for class 2 embryos; and the range from −7 to −15.5 is a "maybe" zone. Other methods could be used to establish such thresholds.

Preimplanted mouse embryos which retain their developmental potential (i.e., class 1 embryos) thus exhibit a steady state transmembrane calcium efflux as measured by the non-invasive, ion-selective vibrating electrode incorporating in this case a calcium ionophore, an efflux that is symmetrical about the embryo with no observed polarity. Embryos with impaired developmental potential, as measured either by a fragmented morphology or subsequent failure to divide (i.e., class 2 embryos), failed to exhibit a steady-state transmembrane calcium efflux. The absence of an equivalent efflux in those embryos which subsequently failed to grow further suggests that the steady state calcium efflux is a viable diagnostic of the health of the embryo.

Subsequent experiments involving the use of hamster embryos have found similar results.

Experiments have also been performed with human oocytes, and have shown that the steady-state transmembrane calcium efflux of an oocyte can be successfully measured in this manner with such a non-invasive calcium-sensitive vibrating probe. In the case of an oocyte, the determination of a threshold or baseline can be made by measuring ion efflux from a group of oocytes, fertilizing the group of oocytes, observing cell division, and correlating the measured ion efflux of the oocytes with the ability of further cleavage after fertilization.

Accordingly, the present invention includes a number of different methods including the following. A number of oocytes can be tested to determine their ion flux, and the oocytes can then be fertilized and monitored to establish a threshold or baseline against which the flux of subsequent oocytes can be compared for developmental potential. This method can also be performed with respect to fertilized embryos as described above, in which case a certain baseline can be established above which the embryos are considered to have developmental potential, and below which they are not. (Note that the terms "above" and "below" are only used in a relative manner even though by convention a higher efflux has a more negative number.)

Having performed one of the methods noted above, a particular oocyte is removed from a female and its steady-state transmembrane ion flux is measured to determine its developmental potential. In another method, an oocyte is removed and is fertilized to produce an embryo whose ion flux is measured to determine its developmental potential. These latter two methods can be performed alternatively, or they can be performed serially such that the ion flux of an oocyte is first measured to determine its developmental potential, and then after fertilization, the ion flux of the resulting embryo is also measured to determine its developmental potential. If the embryo has an ion efflux that indicates sufficient developmental potential, it can be implanted in the female.

Having described an embodiment of the present invention, it should be apparent that modifications can be made without departing from the scope of the present invention. While the present invention has been described with the use of a calcium ionophore to measure calcium efflux, other ionophores can be used to measure efflux other ions, such as potassium. Similar methods of correlating measured efflux against observed cell division, establishing baselines, and performing measurements of subsequent oocytes and/or embryos and comparing them to the baselines can be performed as discussed above.

What is claimed is:

1. A method comprising:

measuring ion flux of a mammalian embryo using a non-invasive probe to derive an ion flux signal which is diagnostic for whether the embryo is morphologically capable of further cleavage; and using the measurement of the ion flux to assess whether the mammalian embryo is morphologically capable of further cleavage.

2. The method of claim 1, wherein the step of measuring includes using a calcium-sensitive vibrating probe.

3. The method of claim 1, wherein the step of measuring includes positioning the probe about 1 micron from the embryo on a number of sides of the embryo.

4. The method of claim 1, wherein the embryo is a human embryo.

5. The method of claim 1, wherein the ion flux being measured is calcium efflux, the method further comprising a step of implanting the embryo in a female in response to a determination that the calcium efflux of the embryo exceeds a threshold.

6. A method comprising:

measuring ion flux using a non-invasive probe to derive an ion flux signal which is diagnostic for whether the oocyte is morphologically capable, upon its fertilization to produce an embryo, of further cleavage; and using the measurement of the ion flux to assess the developmental potential of the mammalian oocyte.

7. The method of claim 6, wherein the measuring step includes using a calcium-sensitive vibrating probe.

8. The method of claim 6, further comprising steps of:

fertilizing the oocyte in vitro; and measuring ion flux of the embryo to determine whether the embryo is morphologically capable of further cleavage.

9. A method comprising the steps of:

measuring ion flux for a number of oocytes using a non-invasive probe to derive a number of ion flux signals;

fertilizing the oocytes to produce embryos;

providing conditions for the embryos to promote cell division; and comparing the measured ion flux signals of the oocytes with the cell division of the embryos to derive a threshold against which the ion flux of subsequent oocytes can be compared to determine potential viability.

10. The method of claim 9, wherein the measuring step includes using a calcium-sensitive probe.

11. A method comprising the steps of:

measuring ion flux for a number of mammalian embryos using a non-invasive probe to derive a number of ion flux signals;

providing conditions for the mammalian embryos to promote cell division; and comparing the measured ion flux signals of the mammalian embryos with the cell division of the mammalian embryos to derive a threshold ion flux signal against which the ion flux of subsequent mammalian embryos can be compared to determine potential viability.

12. The method of claim 11, wherein the measuring step includes using a calcium-sensitive probe.

* * * * *